(12) United States Patent
Babic et al.

(10) Patent No.: US 9,329,164 B2
(45) Date of Patent: May 3, 2016

(54) PROTECTION FROM HYDROPHOBIZING AGENTS

(75) Inventors: Bransilav Babic, Mannheim (DE); Wilhelm Leichner, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 13/446,656

(22) Filed: Apr. 13, 2012

(65) Prior Publication Data

US 2012/0252135 A1 Oct. 4, 2012

Related U.S. Application Data

(63) Continuation of application No. PCT/EP2010/065359, filed on Oct. 13, 2010.

(30) Foreign Application Priority Data

Oct. 15, 2009 (EP) ..................................... 09173175

(51) Int. Cl.
| | | |
|---|---|---|
| *G01N 33/487* | (2006.01) | |
| *B65D 81/26* | (2006.01) | |
| *B01L 3/00* | (2006.01) | |
| *B01L 9/00* | (2006.01) | |

(52) U.S. Cl.
CPC ........ *G01N 33/48778* (2013.01); *B65D 81/266* (2013.01); *B01L 3/5027* (2013.01); *B01L 9/527* (2013.01); *B01L 2300/0825* (2013.01); *B01L 2400/0406* (2013.01); *Y10T 436/255* (2015.01)

(58) Field of Classification Search
None
See application file for complete search history.

(56) References Cited

U.S. PATENT DOCUMENTS

| | | | |
|---|---|---|---|
| 5,505,308 A | 4/1996 | Eikmeier et al. | |
| 5,683,662 A * | 11/1997 | Hollinger, Jr. ................ | 422/291 |
| 6,497,845 B1 | 12/2002 | Sacherer | |
| 2003/0039584 A1 | 2/2003 | Schabbach et al. | |
| 2005/0245954 A1 | 11/2005 | Roe et al. | |
| 2006/0293611 A1 | 12/2006 | Calasso et al. | |
| 2007/0020143 A1 | 1/2007 | Seidenstricker et al. | |
| 2008/0031778 A1 | 2/2008 | Kramer | |
| 2009/0098018 A1 | 4/2009 | Bainczyk et al. | |
| 2009/0198119 A1 | 8/2009 | Niederberger et al. | |

FOREIGN PATENT DOCUMENTS

| | | |
|---|---|---|
| DE | 10 2004 033 317 A1 | 2/2006 |
| EP | 0 640 393 A1 | 3/1995 |
| EP | 0 951 939 A2 | 10/1999 |
| EP | 1 022 565 A2 | 7/2000 |
| EP | 1 736 772 A1 | 12/2006 |
| EP | 1 739 432 A1 | 1/2007 |
| EP | 1 884 188 A1 | 2/2008 |
| EP | 2 093 162 A1 | 8/2009 |
| WO | WO 2005/084530 A2 | 9/2005 |
| WO | WO 2005/104948 A1 | 11/2005 |

OTHER PUBLICATIONS

International Preliminary Report on Patentability; PCT/EP2010/065359; May 10, 2012.
ROMPP Online, Version 3.7, Absorption and Adsorption, at least as early as Sep. 22, 2010 (http://www.roempp.com/prod/roempp.php) (6 pages).
EP 09 17 3175 European Patent Office Search Report dated Dec. 29, 2009 (5 pages) and Translation (2 pages).

* cited by examiner

*Primary Examiner* — Yelena G Gakh
*Assistant Examiner* — Michelle Adams
(74) *Attorney, Agent, or Firm* — Bose McKinney & Evans LLP

(57) ABSTRACT

The present invention concerns storage containers for storing diagnostic elements having a hydrophilic or hydrophilically coated surface. Furthermore, the invention concerns analytical measuring devices which comprise storage containers of this type, and the use of an absorption material for selectively absorbing hydrophobic, volatile substances in such storage containers.

26 Claims, No Drawings

PROTECTION FROM HYDROPHOBIZING AGENTS

RELATED APPLICATIONS

This application is a continuation of PCT/EP2010/065359, filed Oct. 13, 2010, which claims priority to EP09173175.2, filed Oct. 15, 2009, both of which are hereby incorporated by reference in their entireties.

BACKGROUND

The present invention concerns storage containers for storing diagnostic elements having a hydrophilic or hydrophilically coated surface. The present invention additionally concerns analytical measuring devices which comprise storage containers of this type, and the use of an absorption material for selectively absorbing hydrophobic, volatile substances in such storage containers.

Diagnostic elements are important components of clinically relevant analytical methods. This primarily concerns the measurement of analytes, e.g., metabolites or substrates which are determined directly or indirectly for example with the aid of a specific enzyme for the analyte. The analytes are converted with the aid of an enzyme-coenzyme complex and subsequently quantified. In this process the analyte to be determined is contacted with a suitable enzyme and a coenzyme where the enzyme is usually used in catalytic amounts. The coenzyme is physicochemically changed, e.g., oxidized or reduced by the enzymatic reaction and the process is for example detected electrochemically or photometrically. A calibration yields a direct relationship between the measured value and the concentration of the analyte to be determined.

An important criterion when preparing diagnostic elements is their ability to take up a sample containing the analyte. For this purpose, numerous commercially available diagnostic elements comprise a hydrophilic or hydrophilically coated surface which enables the test element to be wetted with the sample and allows the sample to be taken up into the test element for example by means of a sample collection element utilizing capillary effects when the diagnostic test element is contacted with a liquid sample containing the analyte.

Long-term stability has often proven to be a problem with the diagnostic test elements described above. Thus, it is known that metallic sample collection elements derived fresh from the etching bath and having a hydrophilic surface rapidly fill with aqueous liquids such as for example blood.

However, after a short period of exposure to air or after brief storage in conventional packages, the filling time of the sample collection element becomes increasingly longer and ultimately results in a complete loss of its sample take up capability. The filling time can be shortened again to the original level by treating these non-functional sample collection elements with plasma; however, the ability to take up samples is lost again within a few days.

The increasing loss of the ability of sample collection elements to take up a sample of the analyte to be determined, is due to a progressive hydrophobization of the surface of the sample collection elements which in its original state is hydrophilic or hydrophilically coated. This hydrophobization is caused by hydrophobic substances such as, for example, hydrophobic, moderately volatile organic chemical substances that come into contact with the sample collection element.

Packages for diagnostic elements which consists at least partially of plastic have proven to be particularly critical in this connection and are responsible for a significant hydrophobization of hydrophilic surfaces as a result of the slow escape of low-molecular, hydrophobic compounds from the plastic such as for example low boiling solvents or residual monomers. However, in addition to these substances which escape from packaging materials, hydrophobic volatile substances which are used in the production of the diagnostic elements that are to be stored or are formed in this process and are for example contained in the chemical coating of the test elements also result in a hydrophobization of hydrophilically coated surfaces and thus make the sample collection elements which are packaged together with the diagnostic element unusable.

If the diagnostic elements have to be sterilized before use, there is the additional problem that in general damage may be caused to the packaging or/and to the diagnostic element when for example an already packaged diagnostic element is irradiated with ionizing radiation, which subsequently can result again in the generation and release of hydrophobic volatile substances which are able to hydrophobize a hydrophilically coated sample collection element that is stored in the packaging.

In order to avoid a hydrophobization of objects having a hydrophilic surface by the packaging material and thus ensure a high degree of hydrophilicity of the surface over long storage periods, U.S. Publication No. 2009/0198119 suggests the use of a packaging which comprises at least one loose cover or/and at least one adsorbing surface in its interior, the affinity of which for apolar substances is the same as or higher than that of the hydrophilic surface of the object to be stored.

In particular, the aforesaid document envisages the use of adsorber elements or adsorber layers in the form of a hydrophilic coating, the hydrophilicity or surface energy of which is the same or higher than the hydrophilicity or surface energy of the surface of the packaged object, in order to ensure an effective adsorption of the apolar gases to the adsorber layer. In this process, the apolar gases are deposited among others on the hydrophilic surface of the adsorber element or adsorber layer which at least partially protects the hydrophilic surface of the packaged object from hydrophobization. Materials which are suitable for such hydrophilic coatings comprise for example dextran sulfate, lecithin, polyacrylic acids and polyacrylates.

However, the hydrophilic coatings used in U.S. Publication No. 2009/0198119 to adsorb apolar gases have disadvantages. Thus, the packaging described in the above document does not ensure de facto a selective adsorption of hydrophobic substances and hence ultimately cannot adequately protect against a hydrophobization of the hydrophilic surface of an object to be stored in the packaging.

In this connection, the problem arises that, on the one hand, the hydrophilic surface of the object to be stored in the packaging also hydrophobizes to a lesser or greater extent when the affinity of the adsorbing surface for apolar substances is the same as or at least not significantly higher than that of the hydrophilic surface of the object to be stored. Consequently, under such conditions the apolar gases do not preferably or exclusively adsorb to the hydrophilic surface of the adsorber element or adsorber layer.

In particular, the hydrophilic coatings described in U.S. Publication No. 2009/0198119, however, have the disadvantage that they preferably adsorb water (and not apolar gases), due to their high hydrophilicity. If the surface of the adsorber element or of the adsorber layer has a higher hydrophilicity than the surface of the packaged object, then it also has a higher affinity for water than the surface of the packaged object.

In the case of high air humidity, this results in a saturation of the surface of the adsorber element or adsorber layer with water molecules and evaporations from the packaging material can no longer be taken up by the adsorber element or by the adsorber layer, the latter resulting in depositions on the hydrophilic surface of the packaged object and thus in hydrophobization.

SUMMARY AND DETAILED DESCRIPTION

Thus, these teachings are based upon providing a storage container for storing diagnostic elements having a hydrophilic or hydrophilically coated surface with which the disadvantages of the prior art are at least partially eliminated. In particular, this disclosure teaches storing the diagnostic element over a longer period of time without suffering a loss in the hydrophilicity of its surface.

A storage container is disclosed, which comprises
(a) at least one diagnostic element having a hydrophilic or hydrophilically coated surface, and
(b) at least one absorption material for selectively absorbing hydrophobic, volatile substances.

According to this disclosure, the storage container contains at least one absorption material which serves to selectively absorb hydrophobic, volatile substances. The absorption material that is used in the storage containers can be inorganic or organic and comprises any material which enables a selective absorption of hydrophobic, volatile substances. Examples of such absorption materials comprise among others active carbon, controlled porous glass (CPG), silica gels, silicates and alumosilicates (also called aluminosilicates) which are preferably selected from the group consisting of framework silicates and sheet silicates.

The term "selective absorption of hydrophobic, volatile substances" as used in the present application means that the absorption material has a higher affinity for at least one hydrophobic, volatile substance in the sense of the present application than for water under the respective environmental conditions, i.e., at the respective prevailing pressure, the respective prevailing temperature and the respective prevailing air humidity.

As a result of the use of an absorption material which allows a selective absorption of hydrophobic, volatile substances it is possible to specifically separate the hydrophobic, volatile substance(s) from water vapor that is present at the same time in the environment. This means, on the other hand, that the absorption material used cannot be inactivated by a preferential binding of water vapor present in the environment before it has absorbed at least one hydrophobic, volatile substance that is concomitantly present in the environment.

If the absorption material has pores, the pore size of the absorption material described above is designed such that, in the presence of a mixture of at least one hydrophobic, volatile substance and water vapor, preferably the at least one hydrophobic, volatile substance is incorporated into the absorption material such that the absorption material is not saturated due to incorporation of water even at a high relative air humidity. If a porous absorption material is used, this has the additional advantage compared to the adsorber elements or adsorber layers described in U.S. Publication No. 2009/0198119 which each bind apolar gases or/and water vapor only to their surface, that, due to the pores, the absorption capacity of the absorption material for hydrophobic, volatile substances can be considerably increased.

The term "hydrophobic substance" as used within the present application comprises any substance which, due to its chemical structure, exhibits the tendency to not penetrate into water or leave an aqueous phase. In this connection the hydrophobicity is mainly associated with apolar groups such as for example aromatic groups or long-chain hydrocarbon residues which dominate the effect of hydrophilic groups that may additionally be present.

The term "volatile substance" as used within the present application means that the relevant substance has a vapor pressure of $\geq 0.1$ kPa at a temperature of 20° C. Typical examples of volatile substances in the sense of the present application are hydrophobic, organic chemical substances having a molecular weight between 100 and 1000 Daltons.

The use of a naturally-occurring or synthetic silicate as an absorption material has proven to be advantageous within the scope of this disclosure. The term "synthetic silicate" as used herein comprises fully synthetic silicates as well as silicates which are obtained by artificially modifying (e.g. by chemical means) a naturally-occurring silicate. Examples of naturally-occurring or synthetic silicates comprise feldspars, mica, mullite, sillimanite and zeolites but are, however, not limited to these.

The absorption material can be a naturally-occurring or synthetic zeolite in which polyhedra, layers or chains of corner-connected $[(Al, Si)O_4]$ tetrahedra are present which form an anionic spatial network permeated by channels with regularly arranged hollow spaces. Zeolites which are suitable for the purpose of these teachings can be selected by a person skilled in the art according to the respective requirements and particularly comprise (without being limited thereto) medium-pored and large-pored zeolites such as the zeolites that are commercially available under the trade names ZEOflair® 100, ZEOflair® 200 and ZEOflair® 300 (Zeochem, Switzerland).

According to the invention, the absorption material can contain pores which usually have a diameter of about 0.1 nm to about 10 nm. In exemplary embodiments, the absorption material has pores having a diameter of about 0.3 nm to about 1.0 nm, in particular of about 0.5 nm to about 0.8 nm in which an absorption of hydrophobic, volatile substances can take place. The pores of the absorption material preferably have a channel-like or tunnel-like structure which provides a large effective surface that can come into contact with the substances to be absorbed.

The storage containers described in the present application can generally contain the absorption material in any form provided it enables a selective absorption of hydrophobic, volatile substances. The storage container typically contains the at least one absorption material in the form of a separate absorber element or/and integrated into its housing where for example a flat disk or any shaped block can serve as a separate absorber element in the sense of the present invention.

If the storage container contains the absorption material integrated into its housing, this means that the absorption material is incorporated into the solid housing of the storage container and enables at least one inner surface of the storage container to absorb hydrophobic, volatile substances. Such storage containers can for example be manufactured by injection-molding the at least one absorption material into a mold used to manufacture the housing and subsequently cooling/curing the plastic composition.

The size of the particles of the absorption material can be varied according to the respective requirements. Coarse-grained particles having a size of up to several millimeters, i.e., having a size of up to about 5 mm can be used provided that the absorption material is separately added to the inner space of the storage container. In contrast, when the absorption material is mixed into the housing of the storage container, e.g., into a plastic material that is subsequently processed by injection molding, particles that are as fine as possible having a size in the range of ≤1 µm are preferably used.

In a further embodiment, the storage container contains more than one absorption material, i.e. at least two different absorption materials which can differ in their chemical structure as well as with regard to physical parameters such as for example particle size and which are selected by a person skilled in the art according to the respective requirements of the storage container and of the production thereof. The use of several absorption materials has the advantage that a larger range of different hydrophobic substances can be absorbed, said substances differing in their chemical or/and physical properties (e.g. with regard to their molecular size or/and molecular weight) in such a manner that a selective absorption cannot be ensured by a single absorption material.

The storage container contains more preferably a mixture of several absorption materials having different pore diameters. In this connection, a mixture of two absorption materials having different pore diameters has proven to be particularly effective because usually an abundance of different hydrophobic, volatile substances is present in the inner space of the storage container which cannot all be identified or/and examined for their damage potential.

The amounts of absorption material required can vary depending on the type of absorption material as well as on the type and amount of hydrophobic, volatile substances in the storage container and can be adapted to the respective requirements by a person skilled in the art. If, for example, the absorption material used to selectively absorb hydrophobic, volatile substances is introduced into the storage container as a separate absorber element, then the amount of absorption material can be selected without particular regard for the amount of material used to manufacture the storage container. In contrast, in the case of an absorption material integrated into the housing, the storage container contains the absorption material usually in an amount of about 0.5% by weight to about 25% by weight, in particular in an amount of about 1% by weight to about 10% by weight, based on the empty weight of the storage container.

In addition to the at least one absorption material, the storage container additionally comprises at least one diagnostic element having a hydrophilic or hydrophilically coated surface which preferably consists partially or completely of plastic. Thus, in one embodiment it is provided that the storage container comprises several diagnostic elements in the sense of the present application, the term "several" as used herein meaning any number >1, preferably at least 10, more preferably 25 or more.

The diagnostic element can generally be any test element which is suitable for determining the presence or/and the amount of an analyte in a sample. Diagnostic elements which can be stored in the storage container according to the invention comprise for example test tapes, test strips as well as the test elements described in U.S. Publication No. 2009/0198119, which is herewith explicitly incorporated by reference. The diagnostic elements described in the present application each comprise at least one test area that can be brought into contact with a sample containing the analyte and enables a qualitative or/and quantitative determination of the analyte using suitable means.

The term "test tape" as used herein refers to a tape-shaped test element which usually comprises more than one individual test area, preferably at least 10 individual test areas, more preferably at least 25 individual test areas and most preferably at least 50 individual test areas. The individual test areas are preferably each arranged at a distance of a few millimeters to a few centimeters, for example at a distance of <2.5 cm from one another, where the test tape can optionally comprise marker areas between consecutive test areas to detect the distance travelled during tape transport or/and for calibration. Such test tapes are for example described in U.S. Publication No. 2009/0198119, the disclosure of which is herewith explicitly incorporated by reference.

In order to take up liquid samples containing the analyte, the diagnostic elements used may have an element for sample collection or a sample collection element which is either integrated directly into the diagnostic element or can be present separately from this element. An integrated sample collection element within the sense of this disclosure is understood as a device which is physically connected to the diagnostic element and can transfer the collected sample directly onto the test element by suitable means such as for example a capillary channel. In contrast, a separate sample collection element is defined as a sample collection device which is present separate from the diagnostic element and which has no physical connection with the test element. In this case, the sample can for example be transferred onto the diagnostic element after the sample collection device has been returned to a magazine, where the diagnostic element is positioned in the magazine.

Any element can be used as a sample collection element that is able to take up a sufficient amount of sample to determine the analyte and subsequently transfer at least some of the sample onto the actual test element, for example by utilizing capillary effects. In this connection, the use of a needle element having a capillary channel has proven to be particularly advantageous where the needle element preferably consists of a sterilizable material such as for example metal or plastic.

The sample collection element is preferably provided with a hydrophilic coating which is wetted when the sample collection element is brought into contact with a sample containing the analyte, in particular an aqueous sample such as blood and which enables the sample to be taken up into the sample collection element. Numerous materials are known to a person skilled in the art for providing hydrophilic coatings which are preferably both biocompatible and sterilizable. Particularly preferred examples of materials for producing hydrophilic coatings comprise polyacrylic acids, polyacrylates, dextran sulfate, heparin, lecithin and detergents, but are not limited to these.

The storage container of these teachings enables diagnostic elements as described above to be stored for a relatively long period of time or/and at high temperatures without a significant loss of hydrophilicity. In particular, the storage container described herein enables the hydrophilicity of a sample collection element having a hydrophilic coating that is integrated into the diagnostic element or packaged together with the said element to be maintained over a relatively long period of time or/and at elevated temperatures.

As an indicator for this, it is for example possible to use the filling time required to fill the sample collection element with the sample, which filling time continuously increases as the hydrophobization of the hydrophilic surface increases and typically already increases to a value of >1 s (measured for a sample collection element having an inner diameter of 80×120 pm and a filling volume of 40 nl) after a few days for conventionally packaged sample collection elements. In contrast, a sample collection element having corresponding dimensions and packaged according to this disclosure has a considerably shorter filling time of <1 s, preferably a filling time of <0.5 s, in particular a filling time of <0.3 s after storage for nine weeks at a temperature of 35° C.

Alternatively, the hydrophilicity of a sample collection element having a hydrophilic coating can be determined by means of the contact angle or wetting angle which the hydrophilically coated surface of the sample collection element forms with a drop of liquid applied thereon, where deionized water is preferably used as the liquid. Increasing hydrophobization of the hydrophilically coated surface increases the contact angle between this surface of the sample collection element and a drop of water located thereon until finally a hydrophobic or super-hydrophobic surface with a contact angle of ≥90° is formed. In this respect, the application provides in exemplary embodiments that a sample collection element packaged according to this disclosure forms a contact angle of ≤40°, preferably of ≤25°, particularly preferably of ≤10° with a drop of water applied to the hydrophilic coating after storage for nine weeks at a temperature of 35° C.

The diagnostic elements stored by means of the storage container disclosed herein can be used to determine any biological or chemical substance that can be detected photochemically or electrochemically. The analyte is preferably selected from the group consisting of malic acid, alcohol, ammonium, ascorbic acid, cholesterol, cysteine, glucose, glutathione, glycerol, urea, 3-hydroxybutyrate, lactic acid, 5'-nucleotidase, peptides, pyruvate, salicylate and triglycerides, where glucose is particularly preferred. In this connection, the analyte can be derived from any source but is preferably contained in a body fluid comprising but not limited to whole blood, plasma, serum, lymph fluid, bile fluid, cerebrospinal fluid, extracellular tissue fluid, urine as well as glandular secretions such as for example saliva or sweat. The diagnostic elements described herein are preferably used to determine the presence or/and the amount of an analyte in a sample of whole blood, plasma, serum or extracellular tissue fluid.

In one variant, the storage container can additionally comprise at least one desiccant, i.e. at least one absorption material for selectively absorbing water vapour, in addition to the at least one diagnostic element having a hydrophilic or hydrophilically coated surface and the at least one absorption material for selectively absorbing hydrophobic, volatile substances, which can increase the storage life of moisture-sensitive substances of the diagnostic elements described herein such as for example enzymes or/and coenzymes. Absorption materials which are suitable for selectively absorbing water vapour are generally known to a person skilled in the art and for example comprise silica gel and small-pore zeolites, where the term "absorption material for selectively absorbing water vapour" refers to any material which, under the respective environmental conditions, has a higher affinity for water than for a hydrophobic, volatile substance in the sense of the present application.

In another variant, the storage container is free of desiccants. Hence, the storage container described herein enables diagnostic elements having a hydrophilic or hydrophilically coated surface to be stored for a relatively long period of time even without desiccants, for example for a period of at least 2 weeks, preferably of at least 4 weeks and particularly preferably of at least 8 weeks, or/and at elevated temperatures, for example at a temperature of at least 20° C., preferably of at least 25° C. and particularly preferably of at least 30° C., without deposition occurring on the hydrophilic or hydrophilically coated surface of the diagnostic elements due to saturation of the absorption material with water.

In one embodiment, the storage container contains the at least one diagnostic element packed under sterile conditions. For this purpose, a diagnostic element to be sterilized can be introduced into a storage container as described herein in particular before the sterilization, whereupon the storage container is sealed and the diagnostic element can be sterilized in the sealed storage container. The sterile packaging enables the diagnostic element to be kept sterile until later use without requiring a further sterilization. Consequently, these teachings particularly envisage that the diagnostic element is a disposable article which is not used again after use due to loss of sterility.

The sterilization of the diagnostic elements can take place in various ways and preferably comprises ionizing radiation such as for example electron radiation or/and gamma radiation. Since, on the other hand, ionizing radiation often damages the materials that are usually used to manufacture storage containers which, in turn, can generate and release hydrophobic, volatile substances, a particular advantage of the storage containers is their insensitivity towards sterilization-related material damage and the protection of the diagnostic elements stored therein from sterilization-related hydrophobization.

The storage containers described herein can in principle consist of any material that appears suitable for the purposes of storing diagnostic elements having a hydrophilic or hydrophilically coated surface. In one embodiment, the storage container is formed at least partially, i.e. partially or completely, from a material comprising at least one hydrophobic, volatile substance in the sense of the present application, where among others plastics and paper are suitable. The material comprising the at least one hydrophobic, volatile substance is more preferably a plastic, in particular plastics based on or derived from polyamide, polycarbonate, polyester, polyethylene or polypropylene can be used.

The storage containers according to this disclosure generally have any physical form that is familiar to and appears suitable to a person skilled in the art provided that they allow the accommodation of at least one diagnostic element, in particular a test tape or test strip. Exemplary storage containers in the sense of this disclosure comprise in particular blister magazines, leporello magazines, disk magazines, stack magazines and drum magazines which are for example described in EP 0 951 939 A2, EP 1 022 565 A2, EP 1 736 772 A1 and WO 2005/104948 A1. The disclosure of the aforementioned documents is herewith explicitly incorporated by reference, in particular as regards the geometry of the storage containers.

In a further aspect, this disclosure concerns an analytical measuring device which comprises a storage container and is used for the qualitative or/and quantitative determination of an analyte. Examples of such measuring instruments comprise among others the commercially available products Accu-Check® Active, Accu-Chek® Compact and Accu-Chek® Mobile (all Roche Co.) but are not limited to these.

In yet a further aspect, these teachings concern the use of an absorption material for selectively absorbing hydrophobic, volatile substances in a storage container, where the storage container comprises at least one diagnostic element having a hydrophilic or hydrophilically coated surface. With regard to the design of the absorption material, reference is made to the statements made in relation to the description of the storage container according to this disclosure.

It is intended to further elucidate these teachings by the following examples.

EXAMPLES

Example 1

Hydrophobization of Hydrophilically Coated Surfaces by Polymeric Packaging Materials In order to determine the effect of hydrophobic substances escaping from polymeric packaging materials on the filling time of sample collection elements used for diagnostic purposes, microcapillaries having an inner diameter of 80×120 μm and a fill volume of 40 nl (at a length of 4 mm) which had a hydrophilic coating of heparin were stored together with 7.0 g of various commercially available plastics for 9 weeks at 35° C. in each case. Subsequently, the microcapillaries were brought into contact with an anti-coagulated sample of venous blood and the time required to reach a fill height of 4 mm was determined in seconds (n=8). The results are shown in Table 1. "---" in this connection denotes no filling.

TABLE 1

| Plastic | Filling time after 9 weeks at 35° C. [s/4 mm] | | | |
|---|---|---|---|---|
| PET foil pure without beta radiation (comparison) | 0.2 | 0.2 | 0.2 | 0.3 |
| | 0.3 | 0.3 | 0.3 | 0.2 |
| PET foil pure (comparison) | 0.2 | 0.3 | 0.3 | 0.2 |
| | 0.2 | 0.2 | 0.3 | 0.3 |
| Rynite 415HP natural | — | — | — | — |
| | — | — | — | — |
| Rynite 530NC101 natural | 0.4 | 0.8 | 1.1 | 1.1 |
| | — | 0.8 | — | 1.9 |
| Impet 2700GV 1/20 natural | 1.3 | — | — | — |
| | 1.7 | — | — | — |
| Crastin S600F40NC natural | 0.3 | 0.2 | 0.3 | 0.2 |
| | 0.3 | 0.2 | 0.3 | 0.3 |
| Polyester RT6012 transparent | — | — | — | — |
| | — | — | — | — |
| Trogamid CX9704 | 1.4 | — | 0.8 | — |
| | — | — | 1.3 | 1.1 |
| Novodur P2H-AT natural | — | — | — | — |
| | — | — | — | — |
| Novodur P2H-AT black | — | — | — | — |
| | — | — | — | — |
| Makrolon 2405 crystal clear | 0.6 | 0.3 | 0.3 | 0.3 |
| | 0.5 | 0.3 | 0.3 | 0.3 |
| Lustran H604 black | — | — | — | — |
| | — | — | — | — |
| Terlux KR2812 | — | — | — | — |
| | — | — | — | — |
| Finalloy EBC-UC 142UC9B9 | — | — | — | — |
| | — | — | — | — |
| Ticona PET pure polymer | — | — | — | — |
| | — | — | — | — |
| Alu-hotmelt 115-5018 | 0.5 | 0.5 | 0.6 | 0.4 |
| | 0.5 | 0.5 | 0.4 | 0.4 |
| Alu-hotmelt 112-0180 | — | — | — | — |
| | — | — | — | — |
| Alu-hotmelt 112-0433 | — | — | — | — |
| | — | — | — | — |
| PES Ultrason E1010 natural | 0.4 | 0.5 | 0.5 | 0.4 |
| | 1.9 | 0.4 | 0.4 | 0.4 |
| SAN Luran 358 N natural | 1.2 | 0.7 | 0.6 | — |
| | — | 0.8 | — | 0.5 |
| PS polystyrene 145 D | 2.4 | — | 1.5 | 0.8 |
| | — | 2.2 | 1.1 | 1.0 |
| Zeonor 1060 | 0.4 | 0.4 | 0.7 | 0.8 |
| | 0.9 | 0.5 | 0.6 | 0.6 |
| Celanex CX2002 natural | 0.7 | 0.8 | — | 1.1 |
| | 0.6 | 1.1 | — | 1.0 |
| Celanex CX2003 natural | 0.8 | — | 0.5 | 0.6 |
| | — | 0.8 | 0.6 | 0.5 |
| Ultradur S4090 G4 | 0.6 | — | 0.8 | 0.7 |
| | — | 1.3 | 0.5 | — |

As shown by Table 1, the filling time of the microcapillaries is significantly prolonged after storage in the presence of most commercial plastics which in many cases leads to a complete loss of the uptake capacity for sample material, as a consequence of which these plastics are not suitable or are only of limited suitability as a packaging material for diagnostic elements without additional protective measures. In reality, only PET, Crastin® S600F40NC and Makrolon® 2405 still ensure a filling time of <0.5 s after corresponding storage of the microcapillaries, which can be attributed to a small amount of hydrophobic, volatile substances in these commercially available polymers.

Example 2

Reduction of the Hydrophobization of Hydrophilically Coated Surfaces by Volatile Substances from Polymeric Packaging Materials In order to examine the effect of various materials that absorb hydrophobic, volatile substances on the hydrophobization of hydrophilically coated sample collection elements, microcapillaries according to example 1 which were sterilized by means of electron irradiation were stored for 9 weeks at 35° C. in the presence of 7 g Novodur® P2H-AT natural and optionally 1 g absorption material in a PET bag. The results are shown in Table 2.

TABLE 2

| Sample | Filling time after 9 weeks at 35° C. [s/4 mm] |
|---|---|
| microcapillary | 0.24 |
| microcapillary + electron irradiation | 0.22 |
| microcapillary + electron irradiation + Novodur ® | no filling |
| microcapillary + electron irradiation + Novodur ® + ZEOflair ® 100 | 1.15 |
| microcapillary + electron irradiation + Novodur ® + ZEOflair ® 200 | 0.48 |
| microcapillary + electron irradiation + Novodur ® + ZEOflair ® 300 | 0.21 |

As shown by Table 2, sterilization and storage in "clean" packaging (PET bag) does not lead to a loss of the ability to take up sample material. In contrast, in the case of sterilization and storage of the microcapillaries in the presence of Novodur® P2H-AT natural in the absence of an absorption material, a complete loss of the ability to take up sample material is observed (see also Table 1).

Addition of ZEOflair® 100 (pore size 0.56 nm) as an absorption material can partially counteract a hydrophobization of the microcapillaries although a filling time of 1.15 s after 9 weeks storage at 35° C. nevertheless indicates a considerable hydrophobization of the hydrophilically coated surface by hydrophobic substances escaping from the plastic. A significant increase in the protective effect for hydrophilically coated microcapillaries can be achieved by using ZEOflair® 200 (pore size 0.76 nm) as an absorption material, as evidenced by a filling time of 0.48 s. Use of ZEOflair® 300 (mixture of ZEOflair® 100 and ZEOflair® 200) as an absorption material finally achieves an optimal absorption of the hydrophobic substances evaporating from Novodur® P2H-AT natural, as shown by a filling time of 0.21 s after 9 weeks storage at 35° C. The hydrophobic, volatile substances apparently have a non-uniform molecular weight which is why the zeolite mixture that is used gives particularly advantageous results.

Example 3

Reduction of Hydrophobization of Hydrophilically Coated Surfaces Caused by Volatile Substances from Test Elements In order to examine the effect of the test chemistry of conventionally used diagnostic elements on the hydrophobization of hydrophilically coated sample collection elements, microcapillaries according to example 1 were stored for 9 weeks at 35° C. in the presence of 0.92 g carrier material or in the presence of two different compositions (in each case 1.00 g reaction film) used to produce test strips under various conditions in PET bags. The results are shown in Table 3.

TABLE 3

| Sample | Filling time after 9 weeks at 35° C. [s/4 mm] |
|---|---|
| microcapillary (comparison) | 0.235 |
| microcapillary + Pokalon foil 140 μm | 0.300 |
| microcapillary + Accu-Check Active chemical coating | no filling |
| microcapillary + Accu-Check Active chemical coating (previously stored for 3 weeks at 35° C. in the presence of ZEOflair ® 300) | no filling |
| microcapillary + Accu-Chek Active chemical coating + ZEOflair ® 300 | 0.208 |

According to Table 3, the storage of microcapillaries in the presence of carrier material (Pokalon foil) leads to a slight hydrophobization of the hydrophilically coated microcapillaries, as can be deduced from an increase of the filling time from 0.235 s (comparison) to 0.300 s.

In contrast, when the microcapillaries are stored in the presence of an SC-V chemical coating which is that used among others in the commercially available test elements Accu-Chek® Active, Accu-Chek® Compact or Accu-Chek® Mobile (all from the Roche Company), a complete loss of the ability to take up sample material is found due to a strong hydrophobization of the hydrophilically coated microcapillaries, which loss could not be prevented even by a previous three week storage of the test chemistry in the presence of ZEOflair® 300. In the case of a storage of the microcapillaries in the presence of the test chemistry and ZEOflair® 300 as an absorption material, it was possible to completely avoid damage to or hydrophobization of the microcapillaries.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A storage container, comprising:
    a housing;
    at least one diagnostic element configured to detect an analyte contained in a body liquid, the diagnostic element disposed in the housing and having a hydrophilic surface or a hydrophilically coated surface;
    at least one porous absorption material for selectively absorbing at least one hydrophobic, volatile substance, wherein the housing is formed at least partially of a material comprising at least one hydrophobic, volatile substance, wherein said material is selected from plastics and paper; and
    wherein the at least one porous absorption material comprises a mixture of a first porous absorption material defining a first pore size and a second porous absorption material defining a second pore size, the first pore size being approximately 0.56 nm and the second pore size being approximately 0.76.

2. The storage container of claim 1, wherein the at least one absorption material is a naturally occurring or synthetic silicate.

3. The storage container of claim 1, wherein the at least one absorption material comprises zeolite.

4. The storage container of claim 1, wherein the at least one absorption material comprises an absorber element that is separate from and provided in the housing.

5. The storage container of claim 1, wherein the at least one absorption material is integrated into the housing.

6. The storage container of claim 1, wherein the at least one diagnostic element comprises a sample collection element that is integrated into the housing.

7. The storage container of claim 6, wherein the sample collection element comprises a needle element having a capillary channel.

8. The storage container of claim 1, wherein the at least one diagnostic element comprises a sample collection element having a capillary channel.

9. The storage container of claim 8, wherein the sample collection element comprises a needle element.

10. The storage container of claim 8, wherein the sample collection element comprises a hydrophilic coating of one or more of polyacrylic acid, polyacrylate, dextran sulfate, heparin, lecithin and detergent.

11. The storage container of claim 10, wherein the sample collection element forms a contact angle of ≤40° with a drop of water applied to the hydrophilic coating after storage for 9 weeks at a temperature of 35° C.

12. The storage container of claim 10, wherein the sample collection element forms a contact angle of ≤25° with a drop of water applied to the hydrophilic coating after storage for 9 weeks at a temperature of 35° C.

13. The storage container of claim 1, wherein the at least one diagnostic element comprises a test tape or a test strip.

14. The storage container of claim 1, wherein the at least one diagnostic element is sterile-packed.

15. The storage container of claim 1, wherein the storage container does not further comprise a desiccant.

16. The storage container of claim 1, wherein the housing comprises a plastic derived from polyamide, polycarbonate, polyester, polyethylene or polypropylene.

17. The storage container of claim 1, wherein the container comprises a blister magazine, leporello magazine, disk magazine, stack magazine or drum magazine.

18. An analytical measuring device comprising a storage container according to claim 1.

19. A storage container, comprising:
    a housing;
    at least one diagnostic element configured to detect an analyte contained in a body liquid, the diagnostic element disposed in the housing and having a hydrophilic surface or a hydrophilically coated surface;
    at least one absorption material for selectively absorbing at least one hydrophobic, volatile substance, wherein the absorption material has pores with a diameter of at least 0.5 nm; and
    wherein the at least one porous absorption material comprises a mixture of a first porous absorption material defining a first pore size and a second porous absorption material defining a second pore size, the first pore size being approximately 0.56 nm and the second pore size being approximately 0.76 nm.

20. A storage container, comprising:
    a housing;
    at least one diagnostic element configured to detect an analyte contained in a body liquid, the diagnostic element disposed in the housing and having a hydrophilic surface or a hydrophilically coated surface;

at least one porous absorption material for selectively absorbing at least one hydrophobic, volatile substance having a molecular weight of 100 to 1000 Daltons; and wherein the at least one porous absorption material comprises a mixture of a first porous absorption material defining a first pore size and a second porous absorption material defining a second pore size, the first pore size being approximately 0.56 nm and the second pore size being approximately 0.76 nm.

21. A storage container, comprising:

a housing;

at least one diagnostic element configured to detect an analyte contained in a body liquid wherein the analyte is selected from the group consisting of malic acid, alcohol, ammonium, ascorbic acid, cholesterol, cysteine, glucose, glutathione, glycerol, urea, 3-hydroxybutyrate, lactic acid, 5'-nucleotidase, peptides, pyruvate, salicylate and triglycerides; the diagnostic element disposed in the housing and having a hydrophilic surface or a hydrophilically coated surface;

at least one porous absorption material for selectively absorbing at least one hydrophobic, volatile substance, wherein the housing is formed at least partially of a material comprising at least one hydrophobic, volatile substance, wherein said material is selected from plastics and paper; and wherein the at least one porous absorption material comprises a mixture of a first porous absorption material defining a first pore size and a second porous absorption material defining a second pore size, the first pore size being approximately 0.56 nm and the second pore size being approximately 0.76 nm.

22. A storage container, comprising:

a housing;

at least one diagnostic element configured to detect an analyte contained in a body liquid wherein the analyte is selected from the group consisting of malic acid, alcohol, ammonium, ascorbic acid, cholesterol, cysteine, glucose, glutathione, glycerol, urea, 3-hydroxybutyrate, lactic acid, 5'-nucleotidase, peptides, pyruvate, salicylate and triglycerides; the diagnostic element disposed in the housing and having a hydrophilic surface or a hydrophilically coated surface;

at least one absorption material for selectively absorbing at least one hydrophobic, volatile substance, wherein the absorption material has pores with a diameter of at least 0.5 nm; and wherein the at least one porous absorption material comprises a mixture of a first porous absorption material defining a first pore size and a second porous absorption material defining a second pore size, the first pore size being approximately 0.56 nm and the second pore size being approximately 0.76 nm.

23. A storage container, comprising:

a housing;

at least one diagnostic element configured to detect an analyte contained in a body liquid wherein the analyte is selected from the group consisting of malic acid, alcohol, ammonium, ascorbic acid, cholesterol, cysteine, glucose, glutathione, glycerol, urea, 3-hydroxybutyrate, lactic acid, 5'-nucleotidase, peptides, pyruvate, salicylate and triglycerides; the diagnostic element disposed in the housing and having a hydrophilic surface or a hydrophilically coated surface;

at least one porous absorption material for selectively absorbing at least one hydrophobic, volatile substance having a molecular weight of 100 to 1000 Daltons; and wherein the at least one porous absorption material comprises a mixture of a first porous absorption material defining a first pore size and a second porous absorption material defining a second pore size, the first pore size being approximately 0.56 nm and the second pore size being approximately 0.76 nm.

24. A storage container, comprising:

a housing;

at least one diagnostic element configured to detect an analyte contained in a body liquid, the diagnostic element having a hydrophilic surface or a hydrophilically coated surface and wherein the housing is sealed and the diagnostic element is sterile whereby the diagnostic element is adapted to be stored in the housing under sterile conditions prior to use of the diagnostic element;

at least one porous absorption material for selectively absorbing at least one hydrophobic, volatile substance, wherein the housing is formed at least partially of a material comprising at least one hydrophobic, volatile substance, wherein said material is selected from plastics and paper; and wherein the at least one porous absorption material comprises a mixture of a first porous absorption material defining a first pore size and a second porous absorption material defining a second pore size, the first pore size being approximately 0.56 nm and the second pore size being approximately 0.76 nm.

25. A storage container, comprising:

a housing;

at least one diagnostic element configured to detect an analyte contained in a body liquid, the diagnostic element having a hydrophilic surface or a hydrophilically coated surface and wherein the housing is sealed and the diagnostic element is sterile whereby the diagnostic element is adapted to be stored in the housing under sterile conditions prior to use of the diagnostic element;

at least one absorption material for selectively absorbing at least one hydrophobic, volatile substance, wherein the absorption material has pores with a diameter of at least 0.5 nm; and wherein the at least one porous absorption material comprises a mixture of a first porous absorption material defining a first pore size and a second porous absorption material defining a second pore size, the first pore size being approximately 0.56 nm and the second pore size being approximately 0.76 nm.

26. A storage container, comprising:

a housing;

at least one diagnostic element configured to detect an analyte contained in a body liquid, the diagnostic element having a hydrophilic surface or a hydrophilically coated surface and wherein the housing is sealed and the diagnostic element is sterile whereby the diagnostic element is adapted to be stored in the housing under sterile conditions prior to use of the diagnostic element;

at least one porous absorption material for selectively absorbing at least one hydrophobic, volatile substance having a molecular weight of 100 to 1000 Daltons; and wherein the at least one porous absorption material comprises a mixture of a first porous absorption material defining a first pore size and a second porous absorption material defining a second pore size, the first pore size being approximately 0.56 nm and the second pore size being approximately 0.76 nm.

* * * * *